United States Patent
Okerlund et al.

(10) Patent No.: US 7,286,866 B2
(45) Date of Patent: Oct. 23, 2007

(54) METHOD, SYSTEM AND COMPUTER PRODUCT FOR CARDIAC INTERVENTIONAL PROCEDURE PLANNING

(75) Inventors: Darin R. Okerlund, Muskego, WI (US); Hui David He, Brookfield, WI (US); Jerome Knoplioch, Neuilly sur Seine (FR); Jasbir S. Sra, Pewaukee, WI (US); Mark E. Woodford, Waukesha, WI (US)

(73) Assignees: GE Medical Systems Global Technology Company, LLC, Waukesha, WI (US); Jasbir S. Sra, Pewaukee, WI (US)

(*) Notice: Subject to any disclaimer, the term of this patent is extended or adjusted under 35 U.S.C. 154(b) by 378 days.

(21) Appl. No.: 10/063,064

(22) Filed: Mar. 15, 2002

(65) Prior Publication Data

US 2003/0187358 A1    Oct. 2, 2003

Related U.S. Application Data

(60) Provisional application No. 60/337,303, filed on Nov. 5, 2001.

(51) Int. Cl.
*A61B 5/00* (2006.01)
(52) U.S. Cl. ............ 600/407; 600/425; 600/426; 600/427; 600/428; 600/509; 128/920; 128/922; 382/128; 382/131; 382/173; 345/419; 345/420
(58) Field of Classification Search ............ 600/407, 600/424–429, 410, 523, 509; 128/920, 922; 382/128, 130–131, 173; 607/5, 99, 119; 345/419, 420
See application file for complete search history.

(56) References Cited

U.S. PATENT DOCUMENTS

| 3,954,098 | A | 5/1976 | Dick et al. ............ 128/2.05 Z |
| 4,364,397 | A | 12/1982 | Citron et al. |
| 4,574,807 | A | 3/1986 | Hewson et al. ....... 128/419 PG |
| 5,245,287 | A | 9/1993 | Nowak et al. ............ 324/322 |
| 5,274,551 | A | 12/1993 | Corby, Jr. ............ 364/413.13 |
| 5,304,212 | A | 4/1994 | Czeisler et al. ............ 607/88 |

(Continued)

FOREIGN PATENT DOCUMENTS

EP     1182619 A2     2/2002

(Continued)

OTHER PUBLICATIONS

'Advanced Vessel Analysis' product description, http://www.gehealthcare.com/usen/ct/clin_app/products/adwessel.html (printed Dec. 1, 2004).*

(Continued)

*Primary Examiner*—Ruth S. Smith
(74) *Attorney, Agent, or Firm*—Cantor Colburn LLP

(57) ABSTRACT

A method of creating 3D models to be used for cardiac interventional procedure planning. Acquisition data is obtained from a medical imaging system and cardiac image data is created in response to the acquisition data. A 3D model is created in response to the cardiac image data and three anatomical landmarks are identified on the 3D model. The 3D model is sent to an interventional system where the 3D model is in a format that can be imported and registered with the interventional system.

37 Claims, 3 Drawing Sheets

U.S. PATENT DOCUMENTS

| | | | |
|---|---|---|---|
| 5,348,020 A | 9/1994 | Huston | 128/696 |
| 5,353,795 A | 10/1994 | Souza et al. | 128/653.2 |
| 5,391,199 A | 2/1995 | Ben-Haim | 607/122 |
| 5,431,688 A | 7/1995 | Freeman | 607/10 |
| 5,515,849 A | 5/1996 | Murashita et al. | |
| 5,568,384 A | 10/1996 | Robb et al. | 364/419.13 |
| 5,738,096 A | 4/1998 | Ben-Haim | 128/653.1 |
| 5,765,561 A | 6/1998 | Chen et al. | |
| 5,823,958 A | 10/1998 | Truppe | 600/426 |
| 5,839,440 A | 11/1998 | Liou et al. | 128/654 |
| 5,951,475 A | 9/1999 | Gueziec et al. | 600/425 |
| 6,058,218 A | 5/2000 | Cline | |
| 6,081,577 A | 6/2000 | Webber | 372/23 |
| 6,154,516 A | 11/2000 | Heuscher et al. | 378/15 |
| 6,208,347 B1 | 3/2001 | Migdal | 345/419 |
| 6,233,304 B1 | 5/2001 | Hu et al. | 378/8 |
| 6,233,478 B1* | 5/2001 | Liu | 600/428 |
| 6,235,038 B1 | 5/2001 | Hunter et al. | 606/130 |
| 6,246,898 B1 | 6/2001 | Vesely | 600/424 |
| 6,249,693 B1 | 6/2001 | Cline et al. | 600/410 |
| 6,252,924 B1 | 6/2001 | Davantes et al. | 378/8 |
| 6,256,368 B1 | 7/2001 | Hsieh et al. | 378/8 |
| 6,266,553 B1 | 7/2001 | Fluhrer et al. | 600/428 |
| 6,289,115 B1* | 9/2001 | Takeo | 382/130 |
| 6,289,239 B1* | 9/2001 | Panescu et al. | 600/523 |
| 6,314,310 B1 | 11/2001 | Ben-Haim et al. | 600/424 |
| 6,325,797 B1 | 12/2001 | Stewart et al. | 606/41 |
| 6,348,793 B1 | 2/2002 | Balloni et al. | 324/309 |
| 6,353,445 B1 | 3/2002 | Babula et al. | 345/733 |
| 6,381,485 B1 | 4/2002 | Hunter et al. | 600/407 |
| 6,389,104 B1 | 5/2002 | Bani-Hashemi et al. | 378/98.12 |
| 6,411,848 B2 | 6/2002 | Kramer et al. | 607/9 |
| 6,421,412 B1 | 7/2002 | Hsieh et al. | 378/9 |
| 6,456,867 B2 | 9/2002 | Reisfeld | 600/407 |
| 6,468,265 B1* | 10/2002 | Evans et al. | 606/1 |
| 6,490,475 B1 | 12/2002 | Seeley et al. | 600/426 |
| 6,490,479 B2 | 12/2002 | Bock | 600/518 |
| 6,504,894 B2 | 1/2003 | Pan | 378/8 |
| 6,549,606 B1 | 4/2003 | Vaillant et al. | 378/4 |
| 6,556,695 B1 | 4/2003 | Packer et al. | 382/128 |
| 6,584,343 B1 | 6/2003 | Ransbury et al. | 600/509 |
| 6,650,927 B1* | 11/2003 | Keidar | 600/424 |
| 6,950,689 B1 | 9/2005 | Willis et al. | |
| 7,047,060 B1 | 5/2006 | Wu | |
| 2002/0010392 A1 | 1/2002 | Desai | 600/374 |
| 2002/0042570 A1 | 4/2002 | Schaldach et al. | |
| 2002/0046756 A1 | 4/2002 | Laizzo et al. | 128/899 |
| 2002/0138105 A1 | 9/2002 | Kralik | 607/9 |
| 2003/0018251 A1 | 1/2003 | Solomon | 600/427 |
| 2003/0023266 A1 | 1/2003 | Borillo et al. | 606/200 |
| 2003/0028182 A1 | 2/2003 | Sanchez et al. | 606/34 |
| 2003/0097219 A1 | 5/2003 | O'Donnell et al. | 702/19 |
| 2003/0120264 A1 | 6/2003 | Lattouf | |
| 2003/0220557 A1* | 11/2003 | Cleary et al. | 600/409 |
| 2004/0027347 A1 | 2/2004 | Farsaie | 345/419 |
| 2004/0087850 A1 | 5/2004 | Okerlund et al. | 600/407 |
| 2004/0225212 A1 | 11/2004 | Okerlund et al. | 600/407 |
| 2004/0225328 A1 | 11/2004 | Okerlund et al. | 607/9 |
| 2004/0225331 A1 | 11/2004 | Okerlund et al. | 607/14 |

FOREIGN PATENT DOCUMENTS

| | | | |
|---|---|---|---|
| EP | 1321101 A2 | | 12/2002 |
| WO | 9107726 | * | 5/1991 |
| WO | WO91/07726 | | 5/1991 |
| WO | WO96/10949 | | 4/1996 |

OTHER PUBLICATIONS

'CardIQ' product description, http:/ egems.gehealthcare.com/ geCommunity/europe/flex_trial/aw/FlexTrial/aw3_1/eflextrial (printed Dec. 1, 2004).*

"Tiny Device Blocks Unless Part of Heart, Prevents Blood Clots," Apr. 9, 2002; found at www.americanheart.org/presenter. jhtml?identifier=3001890.

"Operating in 3-D," Harvard Medical Alumni Bulletin, Ellen Barlow, found at www.med.harvard.edu/publications/HMAB/ 196fo3d.html.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

W. M. feinberg, J. L. Blackshear, A. Laupacis, R. Kronmal, and R. G. Hart; "Prevalence, Age Distribution, and Gender of Patients with Atrial Fibrillation;" Arch Intern Med., vol. 155, Mar. 13, 1995; pp. 469-473.

M. Haissaguerre, P. Jais, S. C. Shah, A. Takahashi, M. Hocini, G. Quiniou, S. Garrigue, A. Le Mouroux, P. Le Metayer, and J. Clementy; "Spontanrous Initiation of Atrial Fibrillation by Ectopic Beats Originating in the Pulmonary Viens;" The New England Journal of Medicine, vol. 339, No. 10, Sep. 3, 1998; pp. 659-668.

C. Pappone, S. Rosanto, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

"Current Problems in Cardiology- Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, issue 20, Oct. 2001; pp. 1854-1923.

Marchlinski, Francis E. et al., "Linear Ablation Lesions for Control of Unmappable Ventricular Tachycardia In Patients with Ischemic and Nonischemic Cardiomyopathy", Ciculation, 2000: 1288-1296.

Sra, Jasbir et al., "Electroanatomically Guided Catheter Ablation of Ventricular Tarchycardias Causing Multiple Defibrillator Shocks", PACE, Nov. 2001, vol. 24: 1645-1652.

Sra, Jasbir et al., "Feasibility and validation of registration of three-dimensional left atrial models derived from computed tomography with a noncontact cardiac mapping system", Heart Rhythm Society, 2005: 55-63.

C.L. Grines et al.; "Functional Abnormalities in Isolated Left Bundle Branch Block: The Effect of Interventricular Asynchrony," *Circulation*; 1989; 79:845-53.

J. Sra et al., "Noncontact Mapping for Radiofrequency Ablation of Complex Cardiac Arrhythmias;" *J. Interven. Cardia Electrophysiol* 2001; 5:323-331.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Current Problems in Cardiology- Atrial Fibrilliation: Epidemiology, Mechanisms, and Management;" Current Problems in Cardiology, Jul. 2000; pp. 406-524.

PCT Search Report for PCT/US2004/020909.

F. H.M. Wittkampf et al.; "Loca Lisa—New Technique for Real-Time 3-Dimensional Localization of Regular Intracardiac Electrodes;" *Circulationh*; 1999; 99: 1312-1317.

Sra et al., "Registration of Three-Dimensional Left Atrial Computed Tomographic Images With Projection Images Obtained Using Fluoroscopy", Circulation 2005; 112:3763-3768.

Heart Rhythm, "Feasibility and validation of registration of three-dimensional left atrial models derived from computed tomography with a noncontact cardiac mapping system", Jan. 2005, vol. 2, No. 1, pp. 55-63.

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21 (9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

"Tiny Device Blocks Unless Part of Heart, Prevents Blood Clots," Apr. 9, 2002; found at www.americanheart.org/presenter.jhtml?identifier=3001890.

"Operating in 3-D," Harvard Medical Alumni Bulletin, Ellen Barlow, found at www.med.harvard.edu/publications/HMAB/196fo3d.html, no date available.

Toshiko Nakai, Michael D. Lesh, Edward P. Gerstenfeld, Renu Virmani, Russell Jones and Randall J. Lee; "Percutaneous Left Atrial Appendage Occlusion (PLAATO) for Preventing Cardioembolism: First Experience in Canine Model", Circulation 2002; 105;2217-2222; originally published online Apr. 15, 2002; American Heart Association; http://circ.ahajounals.org/cgi/content/full/105/18/2217.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" *Circulation* 1996; 94:407-24.

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S. Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter;" *Paceing Clin. Electrophysiol* 2000; 23:1479-92.

R.J. Schilling et al.; "Simultaneous Endocardial Mapping in the Human Left Ventricle Using a Noncontact Catheter: Comparison of Contact and Reconstructed Electrograms During Sinus Rhythm;" *Circulation* 1998; 98:997-98.

C. C. Gomick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electrophysiol* 2001; Nov. 11(11):1183-92.

J. Schreieck et al., "Radiofrequency Ablation of Cardiac Arrhythmias Using a Three-Dimensional Real-Time Position Management and Mapping System;" *Pacing Clin. Ekectrophysiol*, Dec. 2002, 25(12):1699-707.

F. Wittkampf et al., "Real-Time, Three-Dimensional, Nonfluoroscopic Localization of the Lasso Catheter," *J. Interven. Cardiac Electrophysioll* 2002, 13:630.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Three-Dimensional Right Atrial Geometry Construction and Catheter Tracking Using Cutaneous Patches;" *J. Interven, Cardiac Electrophysiol*, 2003 14:897.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*; 1989; 79:845-53.

H. B. Xia et al., "Differing effects of right ventricular pacing and left bundle branch block on left ventricular function;" *Br. Heart J.*, 1993; 69:166-173.

S. Cazeau et al., "Effects of Multisite Biventricular Pacing in Patients with Heart Failure and Intraventricular Conduction Delay;" *N. Engl. J. Med.* 2001; 344:873-880.

M. V. Pitzalis et al., "Cardiac Resynchronization Therapy Tailored by Echocardiographic Evaluation of Ventricular Acnchrony;" *J. Am. Coll. Cardiol.* 2002; 40:1615-22.

W. T. Abraham et al., "Cardiac Resynchronization in Chronic Heart Failure;" *N. Engl. J. Med.* 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Non-fluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;"J. Am. Coll. Cardiol 2001; 38:1-47.

D. R. Ney "Volumetric Rendering of Compound Tomography Data: Principles and Techniques;" *IEEE Computer Graphics and Applications*; 1990; 24-32.

N. M. Alpert et al., "The Principal Axes Transformation—A Method for Image Ragistration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quality Considerations;" *Computed Body Tomography*, 1998, Lippincot-Raven, Philadelphia, PA pp. 1-20, no date avail.

Milan Sonka and J. Michael Fitzpatrick (eds); *Handbook of Medical Imaging* vol. 2. *Medical Image Processing and Analysis*; pp. 129-174 & 447-506, no date avail.

W. M. Feinberg et al.; "Prevalence, Age Distribution, and Gender of Patients with Atrial Fibrillation;" *Arch. Intern. Med*. vol. 155; Mar. 1995; pp. 469-473.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology- Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, issue 20, Oct. 2001; pp. 1854-1923.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found www.med.harvard.edu/publications/HMAB/196fo3d.html, no date avail.

* cited by examiner

METHOD, SYSTEM AND COMPUTER PRODUCT FOR CARDIAC INTERVENTIONAL PROCEDURE PLANNING

CROSS REFERENCE TO RELATED APPLICATIONS

This application claims the benefit of U.S. Provisional Application No. 60/337,303, filed Nov. 5, 2001.

BACKGROUND OF INVENTION

The present disclosure relates generally to a method for the planning of cardiac interventional procedures and in particular, to a method for using data created by a medical imaging system in cardiac interventional procedure planning.

Medical diagnostic and imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems and nuclear medicine systems. In many instances, these modalities complement one another and offer the physician a range of techniques for imaging particular types of tissue, organs, physiological systems, and so forth. Health care institutions often dispose of several such imaging systems at a single or multiple facilities, permitting its physicians to draw upon such resources as required particular patient needs.

Modern medical diagnostic systems typically include circuitry for acquiring image data and for transforming the data into a useable form which is then processed to create a reconstructed image of features of interest within the patient. The image data acquisition and processing circuitry is often referred to as a "scanner" regardless of the modality, because some sort of physical or electronic scanning often occurs in the imaging process. The particular components of the system and related circuitry, of course, differ greatly between modalities due to their different physics and data processing requirements.

Medical diagnosis and treatment can also be performed by using an interventional procedure such as atrial fibrillation (AF) intervention. Approximately 2.2 million people in the United States have AF. It is the most common arrhythmia and is the most troublesome. It is currently the number one independent cause of stroke in the United States. The incidences of AF increase with age, rapidly increasing after the age of sixty. In the case of left atrial fibrillation, muscle tissues around any of the four pulmonary veins (PV) which connect to the left atrium (LA) can sometimes generate an extra electrical signal causing AF. One current clinical treatment for this condition is ablation using a special catheter which is positioned into the left atrium to create small lesions by administering heat near the origin of the problematic electrical signal. Ablation therapy is done routinely during open heart surgery in less than one hour, but it is very difficult and timely using the less invasive catheter procedure.

In the example of ablation therapy, the following procedure is typical. First, a catheter is position into the LA, guided by X-ray fluoro, this takes approximately one hour. Next, a crude 3D geometric representation of the LA and PV ostiums (openings) is acquired using 3D positioning information from a special catheter by attempting to "sweep through" the space of the LA. Acquiring a crude 3D geometric representation typically takes about one hour. The next steps are performed in the following order as many times as necessary. A special catheter is used to acquire electrical information from one or more heart cycles and this electrical information is mapped onto the crude 3D geometric representation using interventional system software. The next step is to visualize this map in order to identify the areas of concern which should be treated with ablation. Heat is then administered to create lesions, as the software keeps track of these locations. The last step is to recollect the electrical map to see the effects of the lesions. If necessary to complete the ablation therapy, the process continues with repeating the previous steps starting with using a special catheter to acquire electrical information. The ablation therapy procedure is lengthy and labor intensive.

SUMMARY OF INVENTION

One aspect of the invention is a method of creating 3D models to be used for cardiac interventional procedure planning. Acquisition data is obtained from a medical imaging system and cardiac image data is created in response to the acquisition data. A 3D model is created in response to the cardiac image data and three anatomical landmarks are identified on the 3D model. The 3D model is sent to an interventional system where the 3D model is in a format that can be imported and registered with the interventional system.

Another aspect of the invention is a method for creating 3D models to be used for cardiac interventional procedure planning. Acquisition data is received from a medical imaging system. Cardiac image data is created in response to the acquisition data and a 3D model is created in response to the cardiac image data. Three anatomical landmarks are identified on the 3D model. The 3D model is registered on the interventional system in response to the three anatomical landmarks and the 3D model is visualized on the interventional system.

A further aspect of the invention is a system for creating 3D models to be used for cardiac interventional procedure planning. The system comprises a medical imaging system, an acquisition database in communication with the medical imaging system, an image database, a data, transfer mechanism and a processing device. The processing device is in communication with the data transfer mechanism, the acquisition database and the image database. The processing device includes instructions to create 3D models to be used for cardiac interventional procedure planning. The instructions carry out a method to obtain acquisition data from the medical imaging system where the acquisition data is stored in the acquisition database. Cardiac image data is created in response to the acquisition data where the cardiac image data is stored in the image database. A 3D model is created in response to the cardiac image data and three anatomical landmarks are identified on the 3D model. The 3D model is sent to an interventional system, where the 3D model is in a format that can be registered and imported into the interventional system. The sending is performed using the data transfer mechanism.

Another aspect of the invention is a system for creating 3D models to be used for cardiac interventional procedure planning. The system comprises a medical imaging system, an acquisition database in communication with the medical imaging system, an image database, a data transfer mechanism, an interventional system in communication with the data transfer mechanism and a processing device. The processing device is in communication with the data transfer mechanism, the acquisition database and the image database. The processing device includes instructions to created 3D models to be used for cardiac interventional procedure planning. The instructions carry out a method to obtain acquisition data from the medical imaging system where the acquisition data is stored in the acquisition database. Cardiac image data is created in response to the acquisition data where the cardiac image data is stored in the image database. A 3D model is created in response to the cardiac image data and three anatomical landmarks are identified on the 3D model. The 3D model is sent to an interventional system, where the 3D model is in a format that can be registered and imported into the interventional system. The sending is performed using the data transfer mechanism. The 3D model is received at the interventional system and registered in response to the three anatomical landmarks. The 3D model is visualized on the interventional system.

Another aspect of the invention is a computer program product for creating 3D models to be used for cardiac interventional procedure planning. The product includes a storage medium that is readable by a processing circuit and stores instructions for execution by the processing circuit. The instructions for execution include obtaining acquisition data from a medical imaging system and creating cardiac image data in response to the acquisition data. A 3D model is created in response to the cardiac image data and three anatomical landmarks are identified on the 3D model. The 3D model is sent to an interventional system where the 3D model is in a format that can be imported and registered with the interventional system.

Further aspects of the invention are disclosed herein. The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures.

DETAILED DESCRIPTION

Figure 1:
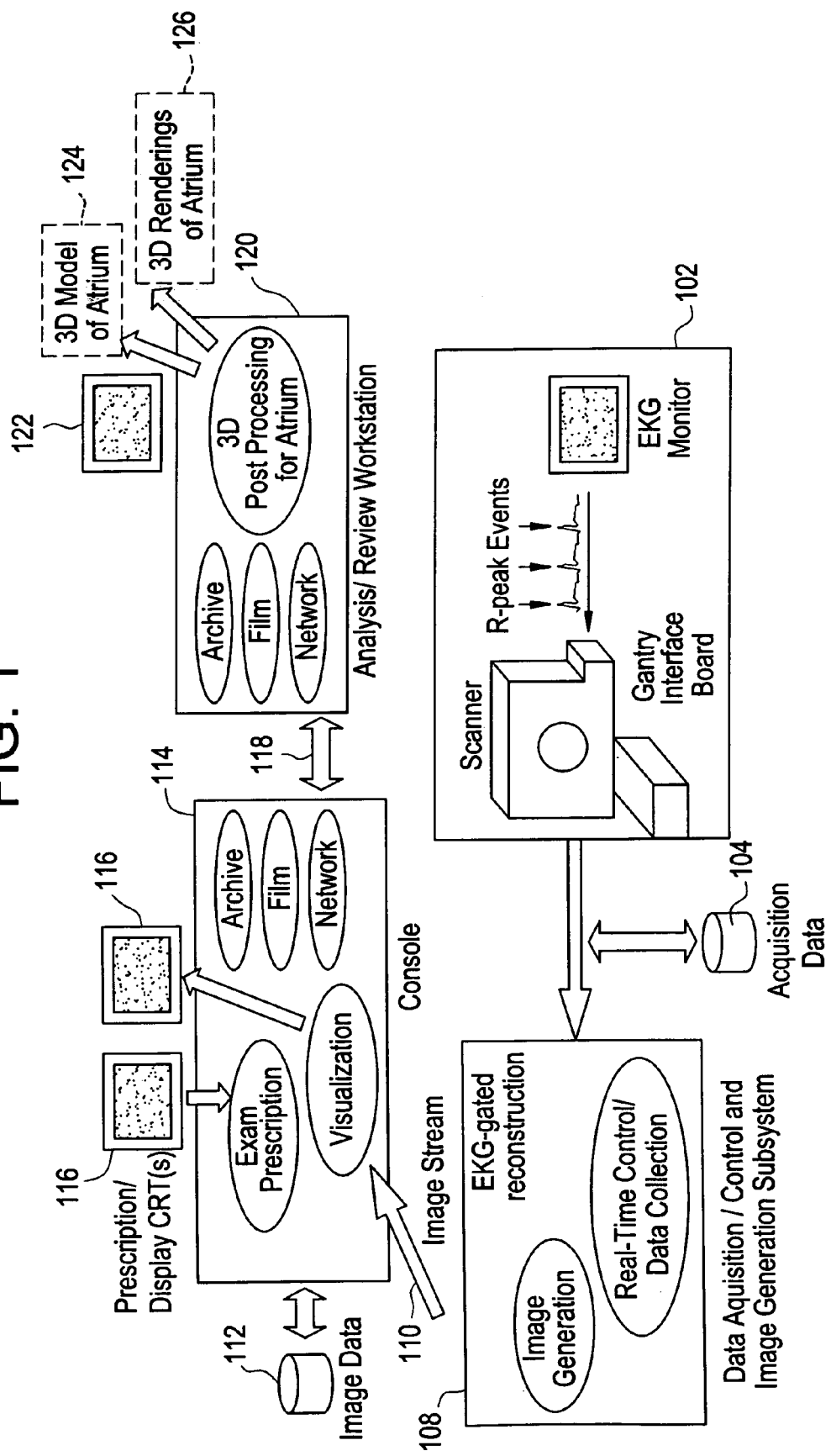
FIG. 1 is an overview of a cardiac computed tomography (CT) system with support for cardiac imaging.

FIG. 1 is an overview of an exemplary cardiac computed tomography (CT) system with support for cardiac imaging. The cardiac CT system is used as an example; other imaging systems known in the art can also be used in an embodiment of the present invention. The scanner portion of the system 102 includes an EKG monitor that outputs R-peak events into the scanner through a scanner interface board. The scanner interface board can be used to couple the EKG system to the scanner. An example of a scanner interface board is a Gantry interface board. The cardiac CT subsystem 102 includes EKG gated acquisition or image reconstruction capabilities to image the heart free of motion in its diastolic phase. Data is output from the scanner into a subsystem 108 that includes software to perform data acquisition, data control and image generation. In addition, data that is output from the scanner, including R-peak time stamps, is stored in the acquisition database 104. In exemplary embodiments, the acquisition database 104 is implemented by a relational database. Acquisition is performed according to one or more acquisition protocols that are optimized for imaging the heart and specifically the left and/or right atrium. Image generation is performed using one or more optimized 3D protocols for automated image segmentation of the CT image dataset for the inner surface of the left and/or right atrium.

Referring to FIG. 1, the image data stream 110 is sent to the operator console 114. The data used by software at the operator console 114 for exam prescription and visualization is stored in an image database 112 along with the data from the image data stream 110. In exemplary embodiments, the image database 112 is implemented by a relational database. Display screens 116 are provided to the operator of the exam prescription and visualization process. The image data may be archived, put on film or sent over a network 118 to a workstation 120 for analysis and review including 3D post processing. The post processing software depicted in the workstation 120 provides immersible views of the atriums (or ventricle chambers), such that the pulmonary veins can be visualized from the inside of the left atrium, for example. These special views can be saved into a 3D rendering of atrium file 126 and viewed by the interventionalist during the intervention procedure. The post processing software also provides for the export of detailed 3D models 124 of the left and br right atriums inner surfaces. In the case of the left atrium, the four pulmonary veins are clearly defined in 3D models 124. The 3D models 124 include anatomical landmarks that can be used for 3D registration with the coordinate system of the interventional or therapeutic system. The 3D models 124 can be in exported in one of several formats: a wire mesh geometric model; a set of contours; a segmented volume of binary images; or a DICOM object using the radiation therapy (RT) DICOM object standard or similar object. Other formats known in the art can also be used to store and export the 3D models 124. Additionally, the operator can view the 3D models 124 on a display screen 122. In another embodiment, the interventional system could contain the advanced 3D registration and/or visualization software included by an embodiment of this invention.

Figure 2:
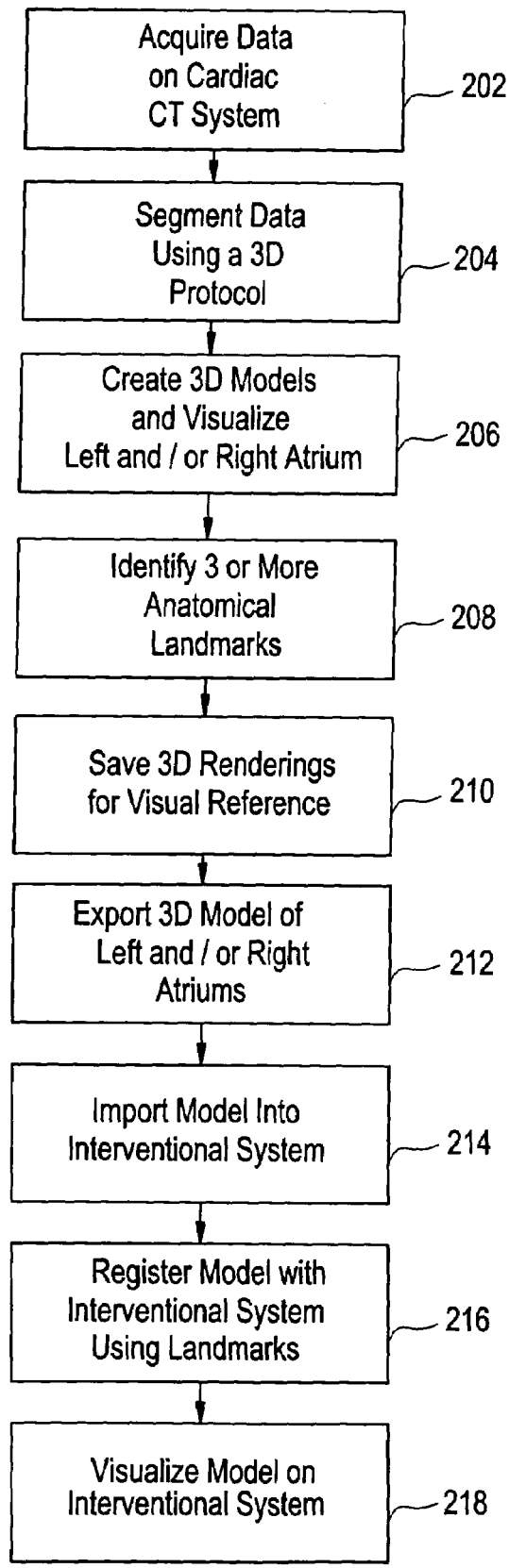
FIG. 2 is a flow diagram of a process where image data created on a cardiac CT is used by an interventional planning system.

FIG. 2 is a flow diagram of an exemplary process where image data created on a cardiac CT is used by an interventional planning system. The process begins at step 202 when a volume of data is acquired on the cardiac CT system using a protocol that is optimized for the left and/or right atrium. An example of a protocol that could be used is a coronary artery imaging protocol that uses a helical scan acquisition technique with gated reconstruction. In an exemplary embodiment, parameters used by the coronary artery imaging protocol could include 0.5 second Gantry periods with 0.375 helical pitch factors using single or multi-sector cardiac reconstruction. Parameters could also include 120 kilovolts, 250 milliamps, and 1.25 millimeters on a multi-slice CT scanner. At step 204, the image dataset is segmented using post processing software that includes a 3D protocol designed to extract the inner surface of the left and/or right atrium. In an exemplary embodiment, post processing software functions can include applying advanced vessel analysis, depositing seeds, using connectivity, and performing region growing techniques. These functions can be performed with a purchased software tool (eg., Advanced Vessel Analysis (AVA)). In an exemplary embodiment, after a tool such as AVA is applied to the image dataset, further processing can include: thresholding, floater filtering, scalpling, bridging data, and scalpling processing. This automated process, at step 204, of segmenting data using a 3D protocol may require one or more queues from the operator. In an exemplary embodiment when a queue is required from the operator the operator may be stepped through the process. The 3D protocol includes default views of the volume and processing steps that can be performed on the data in order to do the 3D segmentation and exporting.

Next, at step 206, the 3D model is created. The left and/or right atrium is visualized using 3D surface and/or volume rendering including an immersible view. A variety of volume rendering software packages are available including Volume Rendering (VR) and Cardiac Image Quality (CARDIQ). At step 208, the operator identifies three or more specific anatomical landmarks to be used for registration with the interventional system. If rigid registration has been used three anatomical landmarks are required. If nonregistration has been used then more than three anatomical landmarks may be required. In the case of the left atrium, the sinus and two superior pulmonary veins could be used. Landmarks can be visualized in a different color scheme than the inner surface of the heart chamber. Alternatively, explicit geometric markers can be inserted into the volume at the landmarks and the chamber can be visualized in a translucent fashion with opaque geometric landmarks. A volume rendering tool such as the one described previously in reference to step 206 can be used to perform this step. In an exemplary embodiment of the invention the operator will be stepped through the visualization and landmark identification.

At step 210, specific 3D renderings that are requested for visual reference during the interventional planning procedure are saved. The 3D renderings could be saved in a variety of manners including DICOM images, on film or in a multimedia format. These views could also be blended with the projection image on a fluoroscopy system. A fluoroscopy system can include positioning an x-ray tube on one side of a patient and a detector on the other side of the patient in order to get real time x-ray images. A fluoroscopy system is an example of one way to guide a catheter during a procedure.

At step 212, a 3D model of the left and/or right atrium is exported using a format of choice. Possible formats include: a wire mesh geometric model; a series of contours; a segmented volume of binary images, and a DICOM object such as the RT DICOM object being used by the radiation therapy DICOM standard. In an exemplary embodiment, all non-relevant data in the binary images are set to zero and the segmented volume of binary images includes only the non-zero information. The value of the voxels correspond to CT attenuation and the density of a tissue expressed in Hounds field units makes up the segmented volume of binary images.

At step 214, the 3D model that has been exported is input to the interventional system. Next, at step 216, the 3D model is registered with the identical landmarks that were identified in step 208. The 3D model can be registered in the coordinate system of the interventional system using rigid or non-rigid registration techniques. At step 218, the model is further visualized on the interventional system and electrical systems are mapped onto the model. The exemplary embodiment described above refers to one 3D model, this could be expanded to any number of 3D models being exported by the cardiac imaging system and imported to the interventional system.

In another embodiment, the process described in FIG. 2 includes an additional step after the interventional procedure has been completed. This step includes importing into the cardiac imaging system both before and after electrical signals calculated by the interventional system to be displayed and archived in a DICOM format. Additionally, the process described in reference to FIG. 2 is applicable to any chamber (eg., left or right atrium, left or right ventricle) or vessel (eg., right coronary artery, ascending aorta) of the heart. Likewise, the process is applicable to ablation or any other type of interventional procedure that requires planning using renderings or 3D models generated by an image acquisition system. The process depicted in FIG. 2 is applicable to other image acquisition systems in addition to a cardiac CT system. For example, if the cardiac images are acquired on an magnetic resonance image (MRI) system, step 204 would include using cardiac segmentation algorithms that are optimized for post processing of magnetic resonance (MR) images.

Figure 3:
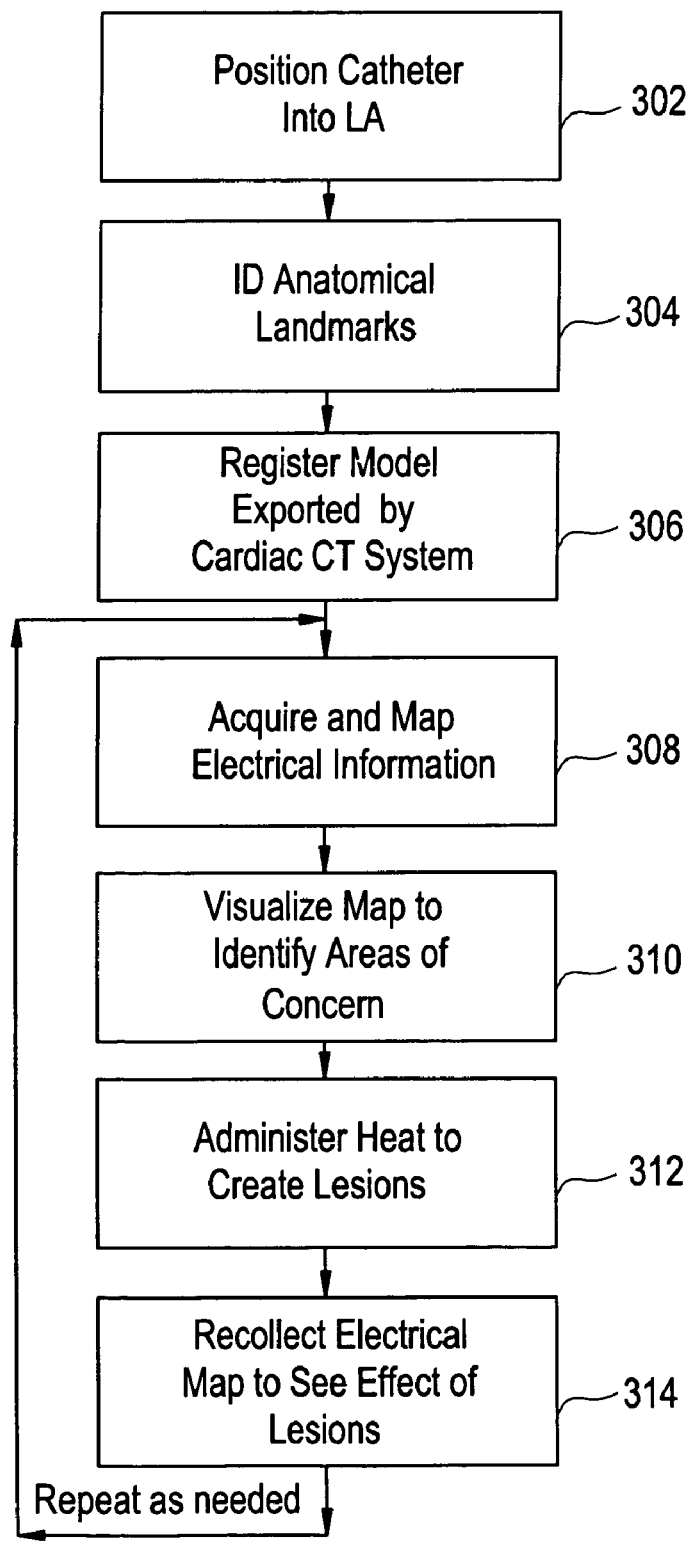
FIG. 3 is a flow diagram of a revised process for performing an interventional procedure.

FIG. 3 is a flow diagram of an exemplary revised process for performing an interventional procedure using an embodiment of the present invention. The revised process for ablation therapy begins at step 302 with positioning the catheter into the left atrium (LA), guided by the x-ray fluoro. This part of the process typically takes about one hour to perform. Next, at step 304, three or more anatomical landmarks are identified within the atrium using a positioning catheter and the fluoro system in order to define a plane. At step 306, the interventional system performs a 3D registration of the 3D model exported by the cardiac CT system such that the model is transformed into the interventional system coordinate system. Steps 304 and 306 replace part of the current interventional procedure described in the background section. Acquiring a crude 3D geometric representation using 3D positioning information from a special catheter by attempting to sweep through the space of the LA is no longer required. Using steps 304 and 306 instead of the current method allows the interventional procedure to be completed in less time.

Next, a loop begins that includes steps 308-314. At step 308, electrical information is acquired from one or more heart cycles using a special catheter. The electrical information is mapped onto the detailed geometric model of the atrium using interventional system software. Next, at step 310, the map is visualized to identify the areas of concern that should be treated with ablation. At step 312, heat is administered to create lesions and the software keeps track of these locations. The electrical map is recollected at step 314 to see the effects of the lesion. This loop, including steps 308A, is repeated as many times as needed to complete the interventional procedure.

The cardiac CT system for atrial fibrillation planning provides information for planning of interventional procedures so that the interventionalist can avoid acquiring a crude 3D geometric representation of the LA and PV ostiums using a special catheter and sweeping through the space of the LA as described in the background section. This can result in the overall duration of the interventional procedure being reduced. Additionally, with a more detailed 3D geometric representation of the LA and PV's than that which could be acquired by a special catheter, fewer iterations of delivering the therapy, steps 308-314 in FIG. 3, are required. The increased accuracy of the geometry can allow the interventionalist to identify the origins of the problematic electrical signals more quickly and with more precision.

Although the preceding embodiments are discussed with respect to medical imaging, it is understood that the image acquisition and processing methodology described herein is not limited to medical applications, but may be utilized in non-medical applications.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method of creating 3D models to be used for cardiac interventional procedure planning, the method comprising:
   obtaining acquisition data from a medical imaging system;
   creating cardiac image data from the acquisition data using a protocol configured for imaging a cardiac chamber;
   creating a 3D model of the cardiac chamber from the cardiac image data;
   identifying three anatomical landmarks on said 3D model;
   inserting three geometric markers at the three anatomical landmarks on the 3D model;
   exporting said 3D model to an interventional system, the 3D model including the geometric markers;
   importing said 3D model with the geometric markers at said interventional system;
   identifying the three anatomical landmarks in a coordinate system of the interventional system; and
   registering said 3D model with the interventional system by transforming the 3D model with the geometric markers to the coordinate system of the interventional system using the three anatomical landmarks.

2. The method of claim 1 further comprising receiving from said interventional system electrical signals calculated before an ablation treatment and electrical signals calculated after the ablation treatment.

3. The method of claim 2 further comprising storing the electrical signals calculated before the ablation treatment and the electrical signals calculated after the ablation treatment in a DICOM format.

4. The method of claim 1 further comprising:
   creating 3D renderings for visual reference in response to said cardiac image data; and
   sending said 3D renderings to said interventional system.

5. The method of claim 4 wherein said 3D renderings are blended with a projection image on a fluoroscopy system.

6. The method of claim 1 wherein:
   said creating cardiac image data is performed using a tool to step an operator through said creating cardiac image data;
   said creating a 3D model is performed using a tool to step an operator through said creating a 3D model; and
   said identifying three anatomical landmarks on said 3D model is performed using a tool to step an operator through said identifying.

7. The method of claim 1 wherein said creating cardiac image data includes:
   segmenting said acquisition data using post processing software that includes a 3D protocol and instructions for extracting an inner surface of the area of interest; and
   visualizing said area of interest including creating an immersible view.

8. The method of claim 7 wherein said post processing software further includes instructions for applying advanced vessel analysis.

9. The method of claim 7 wherein said post processing software further includes instructions for depositing seeds.

10. The method of claim 7 wherein said post processing software further includes instructions for using connectivity, thresholding and morphological operators.

11. The method of claim 7 wherein said post processing software further includes instructions for performing region growing techniques.

12. The method of claim 7 wherein said image is visualized upon the interventional system in a translucent fashion with opaque geometric landmarks.

13. The method of claim 1 wherein said medical imaging system is a cardiac computed tomography system.

14. The method of claim 1 wherein said medical imaging system is a magnetic resonance imaging system.

15. The method of claim 1 wherein said 3D model is in a wire mesh geometric model format.

16. The method of claim 1 wherein said 3D model is in a series of contours format.

17. The method of claim 1 wherein said 3D model is in a segmented volume of binary images format.

18. The method of claim 1 wherein said 3D model is in a DICOM object format.

19. The method of claim 1 wherein said interventional system is an atrial fibrillation intervention system.

20. The method of claim 19 wherein said atrial fibrillation intervention system is used to perform ablation therapy.

21. A method of creating 3D models to be used for cardiac interventional procedure planning, the method comprising:
   receiving acquisition data from a medical imaging system at an interventional system;

creating cardiac image data from the acquisition data using a protocol configured for imaging a cardiac chamber;

creating a 3D model of the cardiac chamber from the cardiac image data;

identifying three anatomical landmarks on said 3D model;

inserting three geometric markers at the three anatomical landmarks on the 3D model;

identifying the three anatomical landmarks in a coordinate system of the interventional system; and registering said 3D model with the interventional system by transforming the 3D model with the geometric markers to the coordinate system of the interventional system using the three anatomical landmarks; and visualizing said 3D model on said interventional system.

22. The method of claim 21 further comprising creating 3D renderings for visual reference in response to said cardiac image data.

23. A system for creating 3D models to be used for cardiac interventional procedure planning, the system comprising:
a medical imaging system;
an acquisition database in communication with said medical imaging system;
an image database;
a data transfer mechanism; and
a processing device in communication with said data transfer mechanism for facilitating:
obtaining acquisition data from said medical imaging system, wherein said acquisition data is stored in said acquisition database;
creating cardiac image data from the acquisition data using a protocol configured for imaging a cardiac chamber, wherein said cardiac image data is stored in said image database;
creating a 3D model of the cardiac chamber from the cardiac image data;
identifying three anatomical landmarks on said 3D model;
inserting three geometric markers at the three anatomical landmarks on the 3D model;
exporting said 3D model to an interventional system, the 3D model including the geometric markers;
importing said 3D model with the geometric markers at said interventional system;
identifying the three anatomical landmarks in a coordinate system of the interventional system; and
registering said 3D model with the interventional system by transforming the 3D model with the geometric markers to the coordinate system of the interventional system using the three anatomical landmarks.

24. The system of claim 23 wherein said processing device includes instructions to implement a method further comprising receiving from said interventional system electrical signals calculated before an ablation treatment and electrical signals calculated after the ablation treatment.

25. The system of claim 23 wherein said processing device includes instructions to implement a method further comprising:
creating 3D renderings for visual reference in response to said cardiac image data; and
sending said 3D renderings to said interventional system.

26. The system of claim 23 wherein said acquisition database is relational.

27. The system of claim 23 wherein said image database is relational.

28. The system of claim 23 wherein said medical imaging system includes:
an EKG;
an interface board receiving R-peak event data from said EKG; and
a scanner in communication with said interface board.

29. The system of claim 23 wherein said data transfer mechanism is a network.

30. The system of claim 29 wherein said network is the Internet.

31. The system of claim 23 wherein said medical imaging system is a cardiac computed tomography system.

32. The system of claim 23 wherein said medical imaging system is a magnetic resonance imaging system.

33. The system of claim 23 wherein said interventional system is an atrial fibrillation intervention system.

34. A system for creating 3D models to be used for cardiac interventional procedure planning, the system comprising:
a medical imaging system;
an acquisition database in communication with said medical imaging system;
an image database;
a data transfer mechanism;
an interventional system in communication with said data transfer mechanism; and
a processing device in communication with said data transfer mechanism, said acquisition database and said image database for facilitating:
obtaining acquisition data from said medical imaging system, wherein said acquisition data is stored in said acquisition database;
creating cardiac image data from the acquisition data using a protocol configured for imaging a cardiac chamber, wherein said cardiac image data is stored in said image database;
creating a 3D model of the cardiac chamber from the cardiac image data;
identifying three anatomical landmarks on said 3D model;
inserting three geometric markers at the three anatomical landmarks on the 3D model;
exporting said 3D model to said interventional system, the 3D model including the geometric markers;
importing said 3D model with the geometric markers at said interventional system;
identifying the three anatomical landmarks in a coordinate system of the interventional system;
registering said 3D model with said interventional system by transforming the 3D model with the geometric markers to the coordinate system of the interventional system using the three anatomical landmarks; and
visualizing said 3D model on said interventional system.

35. The system of claim 34 wherein said processing device, said interventional system and said medical imaging system are physically located in the same geographic location.

36. The system of claim 34 wherein said processing device, said interventional system and said medical imaging system are physically located in more than one geographic location and data is transferred using said data transfer mechanism.

37. A computer program product for creating 3D models to be used for cardiac interventional procedure planning, the product comprising:

a storage medium readable by a processing circuit and storing instructions for execution by the processing circuit for:

obtaining acquisition data from a medical imaging system;

creating cardiac image data from the acquisition data using a protocol configured for imaging a cardiac chamber;

creating a 3D model of the cardiac chamber from the cardiac image data;

identifying three anatomical landmarks on said 3D model;

inserting three geometric markers at the three anatomical landmarks on the 3D model;

exporting said 3D model to an interventional system, the 3D model including the geometric markers;

importing said 3D model with the geometric markers at said interventional system;

identifying the three anatomical landmarks in a coordinate system of the interventional system; and registering said 3D model with the interventional system by transforming the 3D model with the geometric markers to the coordinate system of the interventional system using the three anatomical landmarks.

* * * * *

UNITED STATES PATENT AND TRADEMARK OFFICE
CERTIFICATE OF CORRECTION

| | | |
|---|---|---|
| PATENT NO. | : 7,286,866 B2 | Page 1 of 3 |
| APPLICATION NO. | : 10/063064 | |
| DATED | : October 23, 2007 | |
| INVENTOR(S) | : Darin R. Okerlund et al. | |

It is certified that error appears in the above-identified patent and that said Letters Patent is hereby corrected as shown below:

On the Title page, Item (75), in "Inventors", line 3, delete "sur" and insert -- Sur --, therefor.

On Title page 2, Item (56) under "OTHER PUBLICATIONS", line 17, delete "Spontanrous" and insert -- Spontaneous --, therefor.

On Title page 2, Item (56) under "OTHER PUBLICATIONS", line 20, delete "Rosanto," and insert -- Rosanio, --, therefor.

On Title page 2, Item (56) under "OTHER PUBLICATIONS", line 27, delete "Fibrilliation" and insert -- Fibrillation --, therefor.

On Title page 2, Item (56) under "OTHER PUBLICATIONS", line 34, delete "Ciculation," and insert -- Circulation, --, therefor.

On Title page 2, Item (56) under "OTHER PUBLICATIONS", line 36, delete "Tarchycardias" and insert -- Tachycardias --, therefor.

On Title page 2, Item (56) under "OTHER PUBLICATIONS", line 46, delete "Cardia" and insert -- Cardiac --, therefor.

On Title page 2, Item (56) under "OTHER PUBLICATIONS", line 49, delete "Navication" and insert -- Navigation --, therefor.

On Title page 2, Item (56) under "OTHER PUBLICATIONS", line 51, delete "Fibrilliation" and insert -- Fibrillation --, therefor.

On Title page 2, Item (56) under "OTHER PUBLICATIONS", line 57, delete "Circulationh" and insert -- Circulation --, therefor.

Signed and Sealed this
Twenty-fifth Day of September, 2012

David J. Kappos
*Director of the United States Patent and Trademark Office*

CERTIFICATE OF CORRECTION (continued)
U.S. Pat. No. 7,286,866 B2

On Title page 3, Item (56) under "OTHER PUBLICATIONS", lines 15-20, below "Mar. 2003." delete ""Tiny Device Blocks Unless Part of Heart, Prevents Blood Clots," Apr. 9, 2002; found at www.americanheart.org/presenter.jhtml?identifier=3001890." and ""Operating in 3-D," Harvard Medical Alumni Bulletin, Ellen Barlow, found at www.med.harvard.edu/publications/HMAB/196fo3d.html, no date available.".

On Title page 3, Item (56) under "OTHER PUBLICATIONS", line 39, delete "Paceing" and insert -- Pacing --, therefor.

On Title page 3, Item (56) under "OTHER PUBLICATIONS", line 45, delete "Gomick" and insert -- Gornick --, therefor.

On Title page 3, Item (56) under "OTHER PUBLICATIONS", line 57, delete "Ekectrophysiol," and insert -- Electrophysiol, --, therefor.

On Title page 3, Item (56) under "OTHER PUBLICATIONS", line 61, delete "Electrophysioll" and insert -- Electrophysiol --, therefor.

On Title page 3, Item (56) under "OTHER PUBLICATIONS", line 63, delete "Navication" and insert -- Navigation --, therefor.

On Title page 3, Item (56) under "OTHER PUBLICATIONS", line 8, delete "Acnchrony;" and insert -- Asynchrony; --, therefor.

On Title page 3, Item (56) under "OTHER PUBLICATIONS", line 29, delete "intracaitary" and insert -- intracavitary --, therefor.

On Title page 3, Item (56) under "OTHER PUBLICATIONS", line 38, delete "Compound" and insert -- Computed --, therefor.

On Title page 3, Item (56) under "OTHER PUBLICATIONS", line 42, delete "Ragistration;" and insert -- Registration; --, therefor.

On Title page 3, Item (56) under "OTHER PUBLICATIONS", line 49, delete "Lippincot" and insert -- Lippincott --, therefor.

On Title page 3, Item (56) under "OTHER PUBLICATIONS", line 63, delete "Fibrilliation" and insert -- Fibrillation --, therefor.

On Title page 4, Item (56) under "OTHER PUBLICATIONS", line 8, delete "Fibrilliation" and insert -- Fibrillation --, therefor.

On Title page 4, Item (56) under "OTHER PUBLICATIONS", line 5, delete "'Usless'" and insert -- 'Useless' --, therefor.

CERTIFICATE OF CORRECTION (continued)
U.S. Pat. No. 7,286,866 B2

On Title page 4, Item (56) under "OTHER PUBLICATIONS", line 7, after "found" insert -- at --.

In column 4, line 38, delete "'and br'" and insert -- and/or --, therefor.

In column 6, line 22, before "magnetic" delete "an" and insert -- a --, therefor.